(12) United States Patent
Bonne et al.

(10) Patent No.: US 7,965,089 B2
(45) Date of Patent: Jun. 21, 2011

(54) CHEMICAL IMPEDANCE DETECTORS FOR FLUID ANALYZERS

(75) Inventors: Ulrich Bonne, Hopkins, MN (US);
Fouad Nusseibeh, Champlin, MN (US);
Robert Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/398,890

(22) Filed: Mar. 5, 2009

(65) Prior Publication Data
US 2009/0184724 A1    Jul. 23, 2009

Related U.S. Application Data

(63) Continuation of application No. 11/383,728, filed on May 16, 2006, now Pat. No. 7,518,380.

(60) Provisional application No. 60/681,776, filed on May 17, 2005, provisional application No. 60/743,486, filed on Mar. 15, 2006.

(51) Int. Cl.
*G01R 27/26* (2006.01)
(52) U.S. Cl. ............... 324/663; 324/684; 324/686
(58) Field of Classification Search .......... 324/663
See application file for complete search history.

(56) References Cited

U.S. PATENT DOCUMENTS

| | | |
|---|---|---|
| 4,478,076 A | 10/1984 | Bohrer |
| 4,536,272 A | 8/1985 | Blanchart et al. |
| 4,576,050 A | 3/1986 | Lambert |
| 4,759,210 A | 7/1988 | Wohltjen |
| 4,944,035 A | 7/1990 | Aagardl et al. |
| 5,553,495 A | 9/1996 | Paukkunen et al. |
| 5,852,308 A | 12/1998 | Wood |
| 5,869,749 A | 2/1999 | Bonne et al. |
| 5,889,196 A | 3/1999 | Ueno et al. |
| 6,277,510 B1 * | 8/2001 | Chang et al. .......... 204/293 |
| 6,393,894 B1 | 5/2002 | Bonne et al. |
| 6,792,794 B2 | 9/2004 | Bonne et al. |
| 6,837,118 B2 | 1/2005 | Bonne et al. |
| 7,000,452 B2 | 2/2006 | Bonne et al. |
| 7,518,380 B2 * | 4/2009 | Bonne et al. .......... 324/663 |

(Continued)

FOREIGN PATENT DOCUMENTS
WO    0223134    3/2002

OTHER PUBLICATIONS

Hierlemann, A., et al., "Application-specific sensor systems based on CMOS chemical microsensors", Sensors and Actuators B, V. 70, 2000, p. 2-11.*

(Continued)

*Primary Examiner* — Thomas Valone
(74) *Attorney, Agent, or Firm* — Seager, Tufte & Wickhem LLC

(57) ABSTRACT

A chemical impedance detector having several electrodes situated on or across a dielectric layer of a substrate. The electrodes may be across or covered with a thin film polymer. Each electrode may have a set of finger-like electrodes. Each set of finger-like electrodes may be intermeshed, but not in contact, with another set of finger-like electrodes. The thin-film polymer may have a low dielectric constant and a high porous surface area. The chemical impedance detector may be incorporated in a micro fluid analyzer system.

13 Claims, 19 Drawing Sheets

U.S. PATENT DOCUMENTS

| | | | |
|---|---|---|---|
| 7,776,269 B2 * | 8/2010 | Snow et al. | 422/82.01 |
| 2002/0124631 A1 | 9/2002 | Sunshine et al. | |
| 2004/0224422 A1 | 11/2004 | Bonne et al. | |
| 2004/0259265 A1 | 12/2004 | Bonne | |
| 2005/0042139 A1 | 2/2005 | Bonne | |
| 2005/0059105 A1 | 3/2005 | Alocilja et al. | |
| 2005/0063865 A1 | 3/2005 | Bonne et al. | |
| 2005/0141999 A1 | 6/2005 | Bonne | |
| 2005/0142662 A1 | 6/2005 | Bonne | |
| 2007/0113642 A1 * | 5/2007 | Bonne et al. | 73/204.11 |
| 2009/0184724 A1 * | 7/2009 | Bonne et al. | 324/663 |

OTHER PUBLICATIONS

Patel, S.V. et al., "Chemicapacitive microsensors for volatile organic compound detection" Sensors and Actuators B, V. 96, 2003, p. 541-553 (PDF published article and of higher quality than scanned version in parent U.S. Appl. No. 11/383,790).*

Lide, CRC Handbook of Chemistry and Physics, $82^{nd}$ edition, CRC Press, 2001, p. 13-15.*

Mlsna, T.E. et al., Chemicapacitive microsensors for chemical warfare agent and toxic industrial chemical detection, Sensors and Actuators B, 116, 2006, p. 192-201.*

Horrillo, M.C. et al., Optimization of SAW sensors with a structure ZnO-SiO2-Si to detect volatile organic compounds, Sensors and Actuators B, 118, 2006, p. 356-361.*

Vallance et al., A dielectric study of the glass transition region in segmented polyether-urethane copolymers, Colloid & Polymer Sci., V. 261, 1983, p. 541-554.*

Forsyth, et al., Free volume and conductivity of plasticized polyether-urethane solid polymer electrolytes, J. PHys. Condens. Matter, V. 7, 1995, p. 7601-7617.*

All Art Cited Was Previously Provided in Parent U.S. Appl. No. 11/383,728 Baselt et al., "Design and Performance of a Microcantilever-Based Hydrogen Sensor," Sensors and Actuators B 88, pp. 120-131, 2003.

Bonne et al., "Micro Gas Chromatography Tradeoff Study, Final Report," 54 pages, Nov. 2003.

Bonne et al., "New Gas Composition and Trace Contaminant Sensors," GTI Natural Gas Technologies Conference, Orlando, FL, Sep. 30, to Oct. 2, 2002.

Brown et al., "An Experimental Study of Oscillating Flow with Absorbent Polymers for Use in Respirators," The American Industrial Hygiene Association Journal, May 1996.

Budzien et al., "The Solubility of Gases in Polyethylene: Integral Equation Study of Standard Molecular Models," Macromolecules, vol. 31, No. 19, 11 pages, Sep. 22, 1998.

Cabuz, C., et al., "The Dual Diaphragm Pump," IEEE, pp. 519-522, 2001.

Cabuz, C. et al., "Mesoscopic Sampler Based on 3-DF Arrays of Electrostatically Actuated Diaphragms," Proc. 10th Conf. S.S. S&A. Transducers '99 Jun. 7-12, 1999, Sendai, Japan.

Honeywell Electronic Materials Interconnect Solutions, Thin Films—Dielectrics, Comparison of Solution and Film Properties, Advanced Products for IC Fabrication, 1 page, prior to Jan. 23, 2003.

Stevenson, Robert, "Wintergreen '97," The World of Separation Science, The 19th International Symposium on Capillary Chromatography and Electrophoresis, 11 pages., printed Jul. 22, 2003.

http://www.chrompack.com/cgi/applicsview?ap=A00607&Go=Go, NexTrieve document view, 2 pages, printed Dec. 26, 2002.

Kenndler, Ernst, "Gas Chromatography," Institute for Analytical Chemistry, University of Vienna, pp. 1-34, Sep. 9, 1999.

Lambertus et al., "Design, Fabrication, and Evaluation of Microfabricated Columns for Gas Chromatography," Analytical Chemistry, vol. 76, No. 9, pp. 2629-2637, May 1, 2004.

Patel et al., "Chemicapacitive Microsensors for Volatile Organic Compound Detection," Sensors and Actuators B, 13 pages, 2003.

Phillips, J.B. et al., "Thermal Modulation: A Chemical Instrumentation Component of Potential Value in Improving Portability," Field Analytical Chemistry and Technology, 1(1): 23-29, 1996.

Stanetzek et al., "Chromatographic Characterization of Adsorbents for Selective Sampling of Organic Air Pollutants," American Industrial Hygiene Association Journal, vol. 57, 8 pages, Feb. 1996.

Borman, Better Detector for Plastic Explosives, Chemical, vol. 81, No. 34, 3 pages, Aug. 25, 2003.

Poppe, "Mass Transfer in Rectangular Chromatographic Channels," Journal of Chromatography A, 17 pages, Feb. 22, 2002.

Lide, "CRC Handbook of Chemistry and Physics", CRC Press, 82nd edition, pp. 13-15, 2002.

* cited by examiner

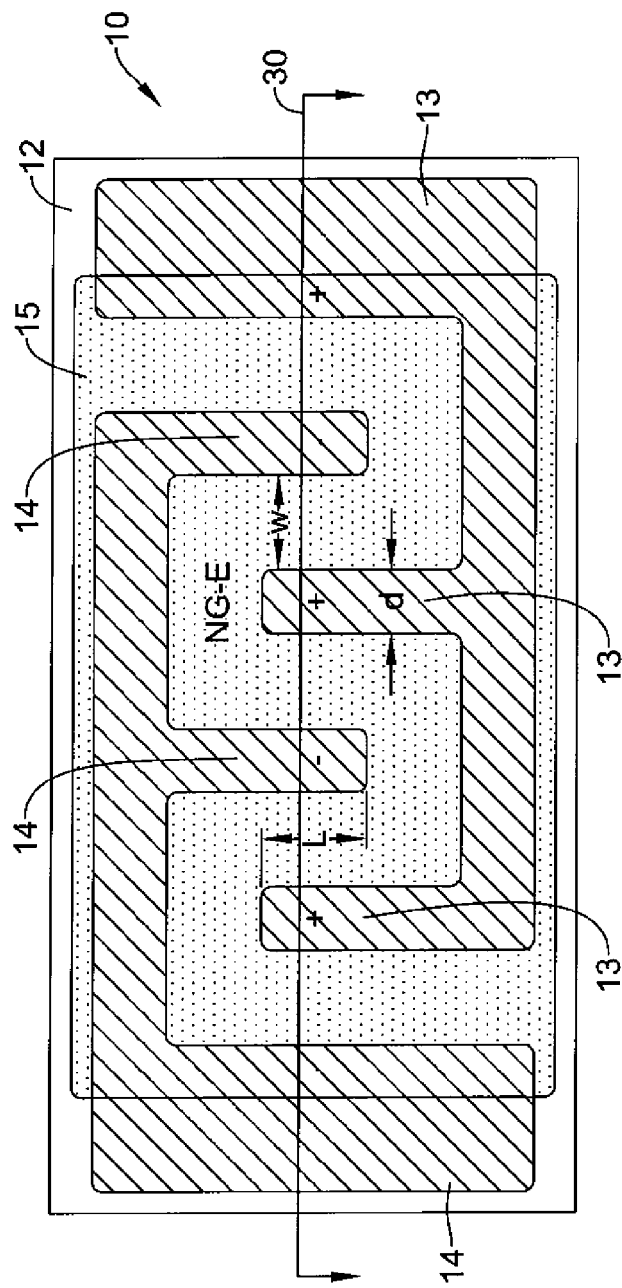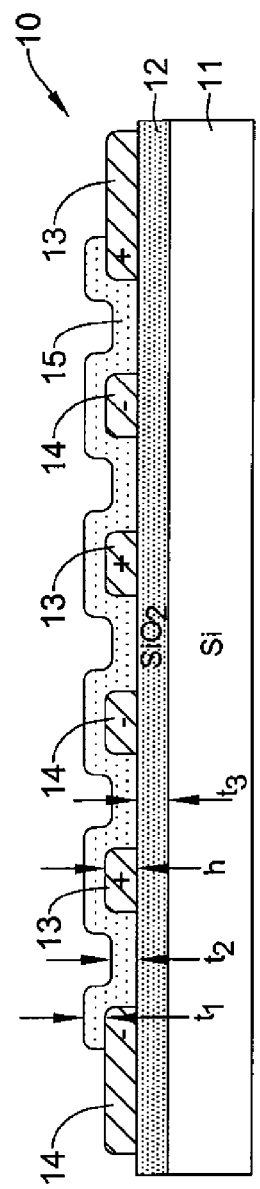
Figure 1A
Figure 1B

| Absorbents | Monomer | $T_{max}$ (°C) | Specific Surface Area (m²/g) | Pore Size (nm) |
|---|---|---|---|---|
| Amberlite XAD-4 | styrene divinylbenzene | 200 | 750 | 5 |
| Tenax GC | 2,6-diphenyl-p-phenylenoxide | 375-400 | 20 | |
| Porapak R | n-vinyl-pyrrolidine | 250 | 450-600 | 72 |
| Amberlite XAD-8 | methacrylic acid | 150 | 140 | 7,6 |
| Activ. charcoal | carbon | >300 | 1000 | 25 |
| Silica gel | silicic acid | 300 | | |
| Silica gel (deactivated) | silicic acid (deactivated) | >250 | | |

*Figure 5*

| Chemical Name | Acronym | Character | Application |
|---|---|---|---|
| Polyisobutylene | PIB | non-polar | non-polar hydrocarbons |
| polydimethyl siloxane | PDMS | | non-polar hydrocarbons |
| poly(diphenoxyphosphazine) | PDPP | slightly basic | |
| polyepichlorohydrin | PECH | more polar | cholroethers |
| bis-cyanoallyl polysiloxane | OV-275 | highly polar | nitro-alkanes, polar VOCs |
| fluoroalcohol | SXFA | acidic without basicity | aromatics, phosphonates |
| cyanopropyl methyl phenylmethyl silicone | OV-225 | | aromatics |

*Figure 6*

| Analyte | LEL (ppm) | IDLH (ppm) | Lowest detected concentration (ppm) | S:N | LOD (ppm) | Polymer used | $\Delta V_{osc}$ (V) |
|---|---|---|---|---|---|---|---|
| Industrial solvents | | | | | | | |
| Acetone | 25000 | 2500 | 11 | 17 | 2 | SXFA | 0.4 |
| Acetonitrile | 50000 | 500 | 25 | 10 | 8 | SXFA | 0.4 |
| Benzene | 12000 | 500 | 142 | 5 | 85 | OV225 | 0.2 |
| Bromobenzene | 5000 | N/A | 7 | 50 | 0.4 | SXFA | 0.4 |
| Ethyl acetate | 20000 | 2000 | 37 | 20 | 6 | SXFA | 0.4 |
| Ethyl alcohol | 33000 | 3300 | 63 | 12 | 16 | SXFA | 0.4 |
| Isopropyl alcohol | 20000 | 2000 | 84 | 18 | 14 | SXFA | 0.2 |
| Methyl alcohol | 60000 | 6000 | 21 | 9 | 7 | SXFA | 0.4 |
| Octane | 14000 | 1000 | 49 | 5 | 29 | OV225 | 0.2 |
| Tetrahydrofuran (THF) | 20000 | 2000 | 7 | 15 | 1 | SXGA | 0.4 |
| Toluene | 11000 | 500 | 61 | 3.3 | 55 | OV225 | 0.2 |
| Chemical warfare agent simulants | | | | | | | |
| Chloroethylether (CEE) | N/A | N/A | 1 | 3 | 1 | PECH | 0.5 |
| | | | 0.4 | 3 | 0.4 | PEVA | 1.0 |
| | | | 0.2 | 10 | 0.06 | SXFA | 0.4 |
| | | | 2.2 | 10 | 0.07 | OV275 | 0.075 |
| Diisopropyl methylphosphonate (DIMP) | N/A | N/A | 0.1 | 100 | 0.003 | SXFA | 0.4 |
| Dimethyl methylphosphonate (DMMP) | N/A | N/A | 0.18 | 300 | 0.002 | SXFA | 0.4 |
| Explosives byproducts and impurities | | | | | | | |
| Nitro-benzene | N/A | N/A | 0.02 | 13 | 0.005 | SXFA | 0.2 |
| | | | 0.44 | 10 | 0.1 | OV275 | 0.075 |
| Nitro-propane | N/A | N/A | 5 | 25 | 0.6 | SXFA | 0.4 |
| Nitro-toluene | N/A | N/A | 0.001 | 23 | 0.0001 | SXFA | 0.2 |

*Figure 7*

Model of Porous Polymer CID Capacitance Signal for MGA's, for K=1 and x=1

Inputs:

Thin-Film:

| | σ, Wt.-Spec. Area cm2/g | εp, Dielectric Constant - | t2 Thickness cm | W, Width cm | | Substr.Mat Silica |
|---|---|---|---|---|---|---|
| | 8,000,000 | 2.26 | 0.00001 | 0.0001 | | εs, Substr. Diel.Const. |
| Electrodes: | N,Num.Fingers - | L,Length cm | h,Height cm | d, Size cm | | 3.826 |
| | 1000 | 0.01 | 0.00001 | 0.0001 | | t3, Substr. Thickness cm |
| Analyte: | Thickness of Monomol.F. cm | εa, Liq.Diel. Constant - | p,Liquid Vapor g/cm3 | Diel.Const. Vacuum F/cm | | 0.0001 |
| | 6.00E-08 | 4 | 1 | 0.0886 | | μ, Max.Analyte Monomol.Film Mass Fraction - |
| Capacitance Materials - | Analyte Concentration ppm | | Max.Analyte Signal,ΔC pF | Electroded Area mm2 | | 0.48 |
| | 0 | | 0.004 | 0.0500 | 0.204 | K, Partition Fct. - |
| C', Vacuum | 0.0886 | | | Background | 1.7119 | Δm(film)/(V(Film)xp(vap)) |
| Co, Film | 0.2002 | | | | 34.2 | 120 |
| C, Film+Gas | 0.2502 | | | | | |
| Cs, Electrodes | 1.7119 | | | | | |
| Stray Capacitance/Signal Cap. Ratio= | | | | | | |

*Figure 8*

| VAPOR/POLYMER | PDMS | PECH | Latex | PDMS/ABACD | SEB | DB-5** | TEMP |
|---|---|---|---|---|---|---|---|
| DMMP | 10,000 | 100,000 | 10,000 | 40,000 | | | |
| Toluene | 1,000 | 2,000 | | | | | |
| DEEP | | | | | | 22,230 | 25°C |
| Decane | | | | | 1,500 | 10,312 | 25°C |
| Toluene | | | | | | (3,458) | 25°C-estimated |
| DMMP | | | | | | 2,618 | 25°C |
| Hexane | | | | | | 167 | 25°C |

*Figure 10*

| Analyte | Monomol. film. thickness t4 cm | Boiling Pt.Temp. T K | Analyte density Liquid pLa g/cm3 | Analyte density gas pga g/cm3 | Dielectric Constant | Partition Function Values σ·t4·ps·pLa/pga K at B.P. | Partition Function Values σ·t4·ps·pLa/pga K at 22°C |
|---|---|---|---|---|---|---|---|
| Hypo-thetical | 6.0·10-8 | | 1.0 | 0.001 | | | 120 |
| Hexane | 4.5·10-8 | 341.8 | 0.6505 | 0.003833 | 2.02 | 39.7 | 124 |
| Octane | 5.5·10-8 | 399.7 | | | 1.9 | | |
| Decane | 7.5·10-8 | 447.3 | 0.7275 | 0.009024 | 2.0 | 35.2 | 9,125 |
| Dodecane | 9.0·10-8 | 489.5 | 0.7457 | 0.01264 | 2.0 | 31.7 | 102,528 |
| Toluene (M/N/pLa)1/3= | 5.6·10-8 | 383.8 | 0.8644 | 0.004186 | 2.4 | 80.0 | ~3,000 |
| Octanol | 5.x·10-8 | 440 | 0.xxxx | 0.00xxxx | 5.1 | xx.0 | |
| Propanol | | | | | 22.0 | | |
| Chloroethyl ether | | | | | 7.4±1.1 | | |

*Figure 12*

| System $u_m(d/D)=v_{min}$ | $v_{min}$ | $h_{min}$ | $SE=h^2\Phi$ |
|---|---|---|---|
| OT | 6.5 | 0.62 | 12.1 |
| BTNE | 5.1 | 0.79 | 7.4 |
| BT256 | 3.0 | 1.30 | 21.0 |
| BT16 | 3.1 | 1.28 | 20.4 |
| BT1 | 4.8 | 0.84 | 20.0 |
| BONE | 3.6 | 1.11 | 14.8 |
| BO256 | 2.1 | 1.86 | 41.7 |
| BO16 | 2.2 | 1.80 | 40.5 |
| BO1 | 3.4 | 1.19 | 40.0 with $h(BO1)/h(AL1)=1.5$ |
| AL256 | 1.7 | 2.38 | 67.9 |
| AL16 | 1.9 | 2.15 | 57.7 |
| AL1 | 5.0 | 0.79 | 17.9 |

*Figure 13*

CHEMICAL IMPEDANCE DETECTORS FOR FLUID ANALYZERS

The present application is a continuation of U.S. patent application Ser. No. 11/383,728, filed May 16, 2006, which claims the benefit of U.S. Provisional Application No. 60/681,776, filed May 17, 2005, and the benefit of U.S. Provisional Application No. 60/743,486, filed Mar. 15, 2006. U.S. patent application Ser. No. 11/383,728, filed May 16, 2006, is hereby incorporated by reference.

The U.S. Government may have some rights in the present invention.

BACKGROUND

The present invention pertains to detectors and particularly to detectors for fluid analyzers. More particularly, the invention pertains to chemical impedance detectors.

U.S. patent application Ser. No. 11/383,723, filed May 16, 2006, entitled "An Optical Micro-Spectrometer," by U. Bonne et al., is hereby incorporated by reference. U.S. patent application Ser. No. 11/383,663, filed May 16, 2006, entitled "A Thermal Pump," by U. Bonne et al., is hereby incorporated by reference. U.S. patent application Ser. No. 11/383,650, filed May 16, 2006, entitled "Stationary Phase for a Micro Fluid Analyzer," by N. Iwamoto et al., is hereby incorporated by reference. U.S. patent application Ser. No. 11/383,738, filed May 16, 2006, entitled "A Three-Wafer Channel Structure for a Fluid Analyzer," by U. Bonne et al., is hereby incorporated by reference. U.S. Provisional Application No. 60/681,776, filed May 17, 2005, is hereby incorporated by reference. U.S. Provisional Application No. 60/743,486, filed Mar. 15, 2006, is hereby incorporated by reference. U.S. patent application Ser. No. 10/909,071, filed Jul. 30, 2004, is hereby incorporated by reference. U.S. Pat. No. 6,393,894, issued May 28, 2002, is hereby incorporated by reference. U.S. Pat. No. 6,837,118, issued Jan. 4, 2005, is hereby incorporated by reference. U.S. Pat. No. 7,000,452, issued Feb. 21, 2006, is hereby incorporated by reference. These applications and patents may disclose aspects of structures and processes related to fluid analyzers, including the PHASED (phased heater array structure for enhanced detection) micro gas analyzer (MGA).

SUMMARY

The present invention may be an implementation of chemical impedance (resistive or capacitive) detector of gases or liquids having a low-k porous and permeable, high surface area thin film polymer on interdigitated electrodes having dimensions compatible with micro-channels of micro analyzers. The detector may be integrated into the structure of a micro analyzer.

BRIEF DESCRIPTION OF THE DRAWING

FIGS. 1a and 1b are views of an illustrative structure of a chemical impedance detector having a capacitance from co-planar interdigitated structures;

FIG. 5 is a table of examples of porous materials with measured specific surface area available for general chromatography pre-concentration;

FIG. 6 is an available list of non-porous polymers that are solvent-castable;

FIG. 7 is an available list of materials to show limit of detection levels and immediate danger to life and health levels and a corresponding detection polymer used;

FIG. 8 is a worksheet of a model with porous capacitance information for parameters like those of a micro analyzer;

FIG. 10 lists some numerical results of the toluene and DMMP uptake in several polymers noted with partition equilibria;

FIG. 12 shows a table of parameters including partial function values for various analtyes;

FIG. 13 is reveals information for evaluation of separation performance of general chromatography columns having partial stationary phase coverage;

DESCRIPTION

Figure 2:
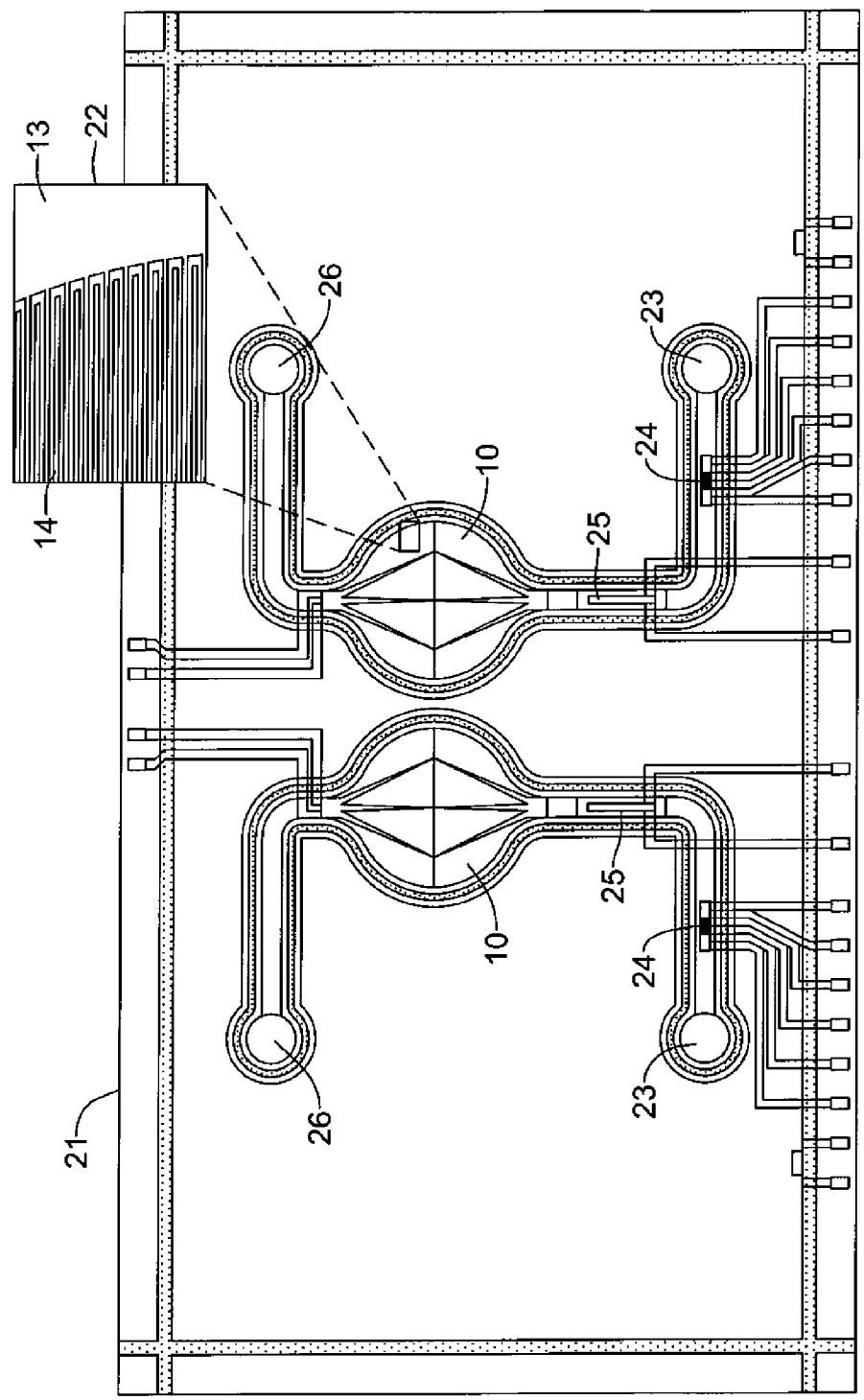
FIG. 2 reveals a differential chemical impedance detection system with co-planar interdigitated electrodes, implemented into a micro analyzer having flow sensors and thermal conductivity detectors.

Related art CIDs (chemical impedance detectors), i.e., polymer gas chromatography (GC) detectors, appear to be bulky, slow (about 1 second), of low sensitivity and not integrated into the structure of the micro analyzers. Such detectors, whether based on changes in resistivity, dielectric constant or strain of the polymer, should achieve a gas-to-solid solution equilibrium, which is either too slow (for high-speed GC applications), due to the slow rate of diffusion into the polymer lattice, or too insensitive, due to low film thickness required if the response time is to be lowered.

FIGS. 1a and 1b show an illustrative example of an interdigitated capacitive polymer detector 10, viz., a chemical impedance detector (CID). FIG. 1a reveals a top view and FIG. 1b shows a cross-section view of the detector 10 at line 30 of FIG. 1a. A layer 12 of dielectric may be situated on a substrate 11. For an illustrative example, the substrate 11 may be silicon and layer 12 may be $SiO_2$. Substrate 11 and layer 12 may be of some other appropriate material. On the $SiO_2$ layer 12 may be finger-like electrodes 13 and 14 intermeshed with each other but not in contact with each other. On the electrodes 13 and 14 and the $SiO_2$ layer 12 portions between the electrodes may be a layer 15 of a thin film polymer. The CID 10 may have a larger or even a smaller structure other than the one shown in the Figures.

The CID 10 may solve related-art shortcomings by using low-k-porous, high surface area (for low stray capacitance and high sensitivity) thin-film (for ms-level speed) 15, on interdigitated pairs of low-height and low-width electrodes 13 and 14 (to maximize signal/stray capacitance ratio), compatible with micro-channel dimensions (for short purge times) of a fluid analyzer, such as a phased heater array structure for enhanced detection (PHASED) micro gas analyzer (MGA).

FIG. 2 shows a layout of two CIDs 10 on a chip 21. An insert 22 which is an enlarged area of a CID 10 reveals an interdigitization of the finger-like portions of electrodes 13 and 14. A gas to be detected may enter an inlet 23, and then pass through a three element flow sensor 24 and a thermo conductivity detector 25. From the detector 25 the gas may go through the CID 10 for detection and a determination of a magnitude of an amount of a particular analyte. From there, the gas may exit from CID 10 to the gas outlet 26. Both CIDs 10 may connected and operated in a differential AC-coupled mode where one is exposed to the analyte peaks and the other is not, or to one of a different composition or concentration.

Figure 3:
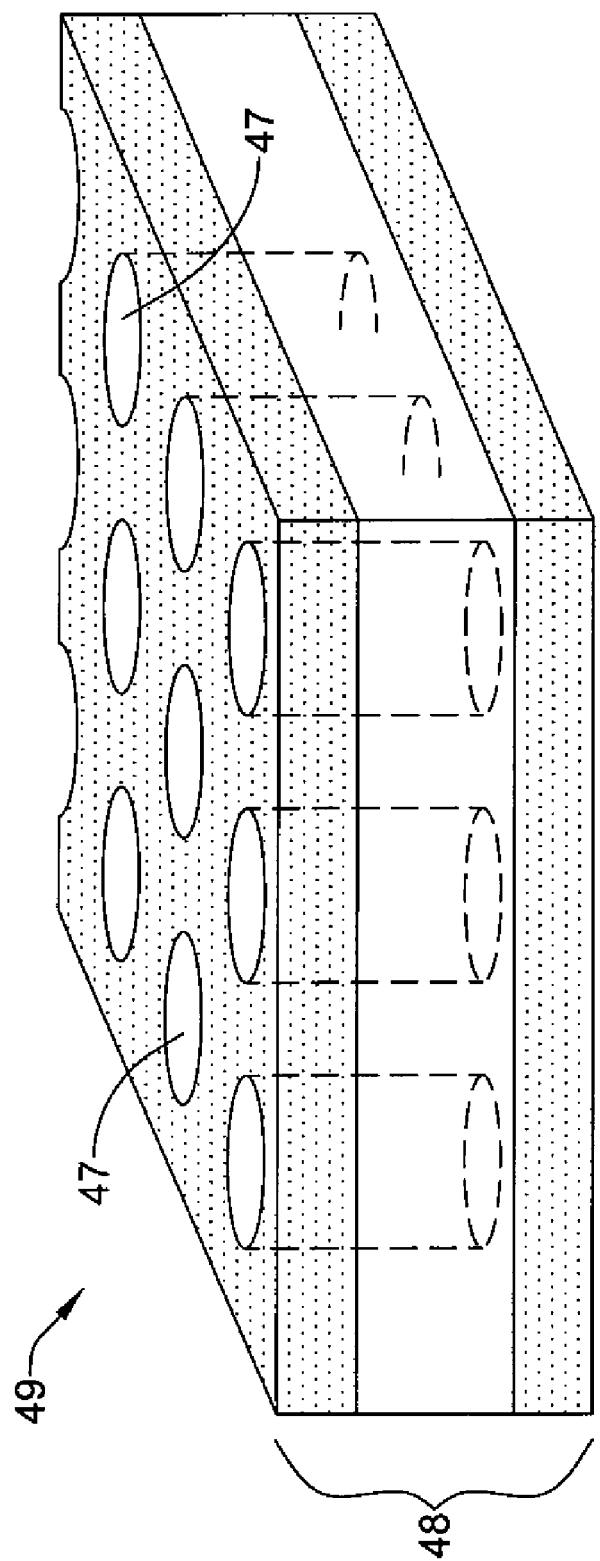
FIG. 3 reveals another capacitive impedance detector structure consisting of an array of holes into a plane-parallel capacitor, with spacings comparable to the thin dielectric, so maximize porosity, sensing signal and analyte access, and minimize response time.

FIG. 3 reveals another capacitive impedance detector structure 49 consisting of an array of holes 47 into a plane-parallel capacitor 48, with spacings comparable to the thin dielectric, so maximize porosity, sensing signal and analyte access, and minimize response time.

Figure 4:
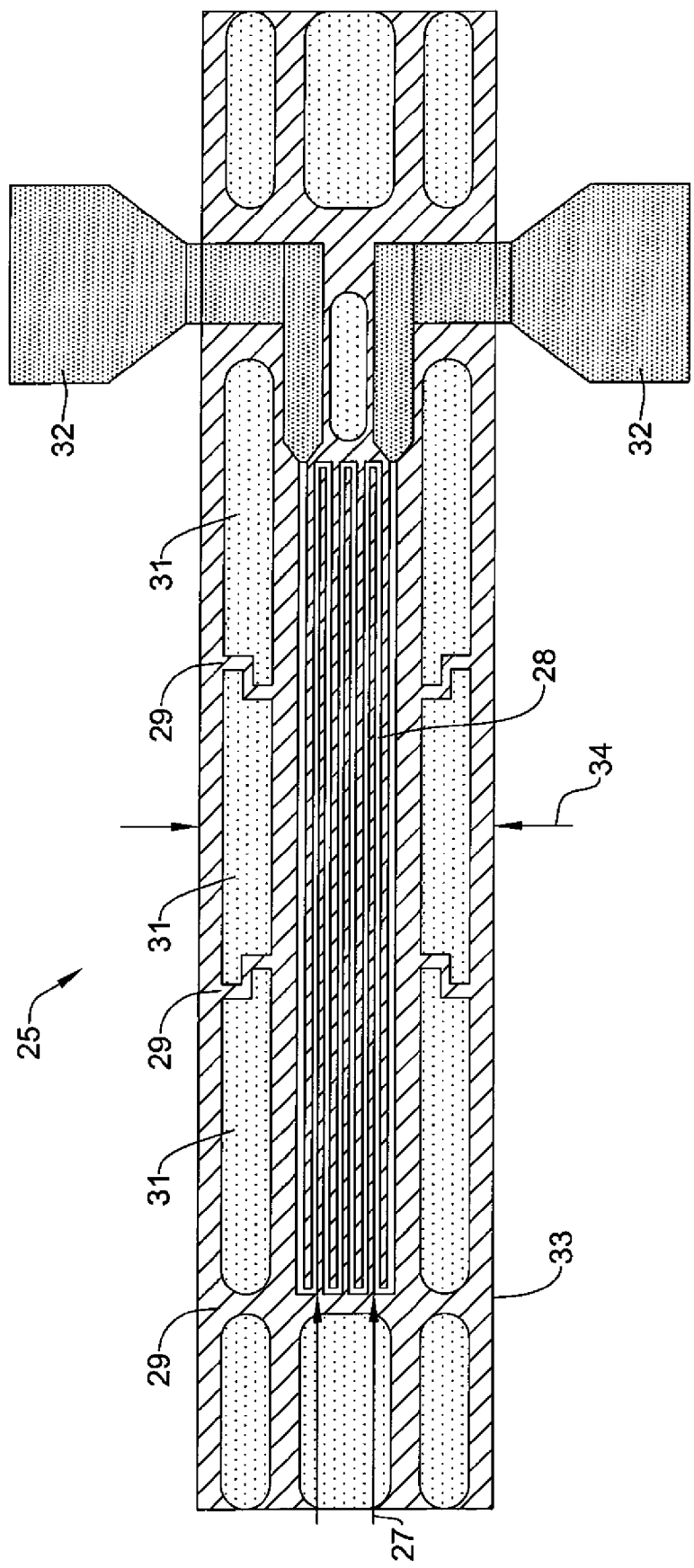
FIG. 4 is a layout of a thermo conductivity detector which may be used in series with a chemical impedance detector on the same analyzer.

FIG. 4 shows a layout of an illustrative example of a thermal conductivity detector (TCD) 25 which may be used in conjunction with the CID 10. A sample gas flow 27 may pass over a detector element 28. The structure of detector 25 may include a wall 33, membrane supports 29 and air gaps 31 on both sides, provided that both sides are sealed relative to the sample analyte being analyzed; otherwise, there would not be air gaps 31 present in the structure of detector 25. Lead-outs 32 may be connected to the detector element 28. Dimension 34 of the detector may be about 100 microns.

Polymer film-based sensors, in general, upon exposure to trace gases, may either change film resistivity, dielectric constant, strain and/or weight. Also, metal oxide films may change resistivity and serve as detectors. The porous, spin-coatable materials may be used for GC pre-concentration and separation. Pre concentration or a pre concentrator may be referred to as concentration or a concentrator, respectively, even though it may be actually like pre concentration or a pre concentrator.

Also, polymer films may be used for gas detection in gas chromatography in the form of SAW detectors (surface acoustic wave, sensitive to changes in film mass). Useful detector results may be obtained with MPN (dodecanethiol monolayer protected gold nanoparticle) films, which change in electrical conductivity when exposed to different gases. These films may have excellent results when used as GC separator films in capillary columns.

A table in FIG. 5 shows examples of porous materials with measured specific surface area used for GC pre-concentration in packed columns but typically not necessarily as solvent-castable films. This table may provide characteristics of selected adsorbents, such as maximum temperature (° C.), specific surface area (m$^2$/g), pore size (nm), and the respective monomer.

A table in FIG. 6 lists non-porous polymers that are solvent-castable. This table provides information relating to detector polymers for solvent casting and stable to 250° C. in inert atmospheres. Films of rubbery (Tg<operating temperature) polymers 100-200 nm in thickness appear to be consistent with fast response times (~milliseconds). A sample gas velocity of 1 m/s may pass a 1-mm long in only about 1 ms. The table of FIG. 6 lists a chemical name, acronym, character and application.

A table in FIG. 7 lists performance in terms of a ppm-level LOD (limit of detection), in relation to the IDLH (immediate danger to life and health) or ppm-level of IDLH, for an analyte detector of industrial solvent vapors, CWA (chemical warfare agent) simulants and ERCs (explosives-related compounds), along with the polymer used for detection. The table may reveal a LEL (lower explosive limit) and an IDLH concentration for selected VOCs (volatile organic compounds), with the lowest detected vapor concentrations and a calculated theoretical LOD in ppm (v/v), signal-to-noise ratio (S:N, measured response in volts/peak-to-peak noise in volts), the polymer used to achieve the lowest detected concentrations, and the oscillation amplitude ($\Delta V_{osc}$).

In order to enable detector performance prediction and comparison between alternate materials, one may define some polymer properties related to their ability to absorb gases: 1) Directly measurable via gas-weight absorption into polymers are partition function values, K, (which are geometry-independent thermodynamic equilibrium values for film materials before and after exposure to analytes); and 2) Also measurable via GC elution or retention times are partition or capacity factors, k'. A comparison between these two is possible by remembering that K=k'·β, where β=volumetric ratio of the gas/film volume of a GC separation column. The values of k'=(t$_r$−t$_o$)/t$_o$ depend on the ratio β and thus on the column ID and film thickness. For example, under otherwise equal conditions, larger ID columns may cause the analyte to reside a greater fraction of the time in the gas phase, and thus be swept through the column within a time closer to that of the unretained analytes, t$_o$, thus resulting in smaller k' values than would be the case with smaller IDs. A similar argument may be made for film thickness. One may herein compare K-values derived from weight gain measurements with GC-derived k' values obtained for a porous film material, in order to estimate likely detector performance.

Another source of K and k' data is provided by theoretical predictions, as can be made via molecule-surface energy interaction models, which can then result in predictions of capacitance detector signal and a film's sensitivity to exposure to given analytes. Such models generate molecular internal energy changes, $\Delta E$, corresponding to the ad- or absorption of a gas molecule on the surface (liquid or gas). The relation between $\Delta E$ and K follows known laws of thermodynamics, which relates changes in $\Delta E$ to changes on enthalpy, $\Delta H$; entropy, $\Delta S$; Gibbs' Free Energy, $\Delta G$; and the equilibrium constant, K: $\Delta H = \Delta E + T\Delta S$; and $\Delta G = -RT\cdot\ln(K) = \Delta H + T\Delta S$.

The present CID 10 two capacitors, for which the capacitance is given by C=N·(Ca+Cd), where Ca=2·$\epsilon_o$·D(k$_1$)/D'(k$_1$) capacitance in air, Cd=2·$\epsilon_o$·$\epsilon_r$·D(y$_1$)/D'(y$_1$) capacitance in the substrate, $\epsilon_o$=0.0886 pF/cm=dielectric constant of vacuum, $\epsilon_r$=relative dielectric constant of the substrate material, D(y), and D'(y) represent the complete elliptic integral of the first kind and its complement, y=W/(W+2s), W the metal width and s the spacing, respectively.

The ratio D(y)/D'(y) is simplified to $$\frac{D(y)}{D'(y)} = \frac{\pi}{\ln\left(2\frac{1+y'}{1-y'}\right)} \text{ for } 0 \le y \le 1/\sqrt{2},$$

$$\frac{D(y)}{D'(y)} = \frac{\ln\left(2\frac{1+y}{1-y}\right)}{\pi} \text{ for } 1/\sqrt{2} \le y \le 1,$$

where $y' = \sqrt{1-y^2}$.

To achieve a response time near 1 millisecond, the plate height and the film thickness (to enable rapid analyte in- and out-diffusion) should be $t_2 \sim h \sim 0.1$ μm, which also requires W to be near that dimension. However, fabrication technology may just allow values of W~1 μm.

Figure 16:
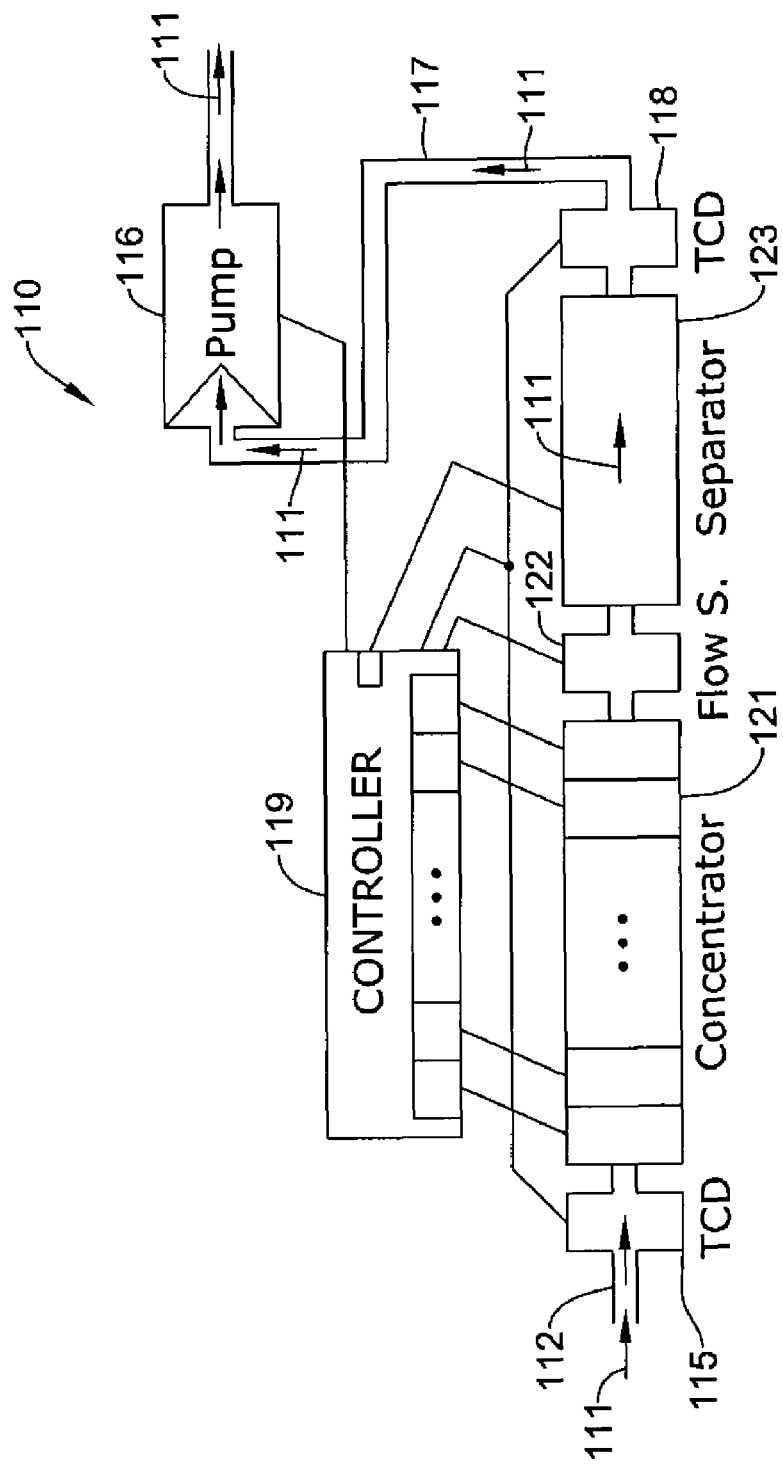
FIG. 16 is a system view of an illustrative phased heater array structure for enhanced detection fluid analyzer which may encompass the present channel and thermal conductivity detector.

FIG. 8 lays out a model of porous capacitance information for parameters like those of a micro analyzer, such as a PHASED MGA 110 (FIG. 16). The above calculations may be compiled into a table in FIG. 8, where the data input cells are highlighted with dashed-line boxes and the CID outputs (signal and background) and results in dotted-line boxes, for a simple alkane such as hexane. Larger molecular weight and more dense analytes may lead to larger ΔC signals. Note, however, that these may be generally maximum ΔC estimates, based on assumption that the analyte concentration on the polymer 15 would be one monomolecular layer, while ignoring gas-phase analyte concentrations and equilibrium partitions.

Figure 9:
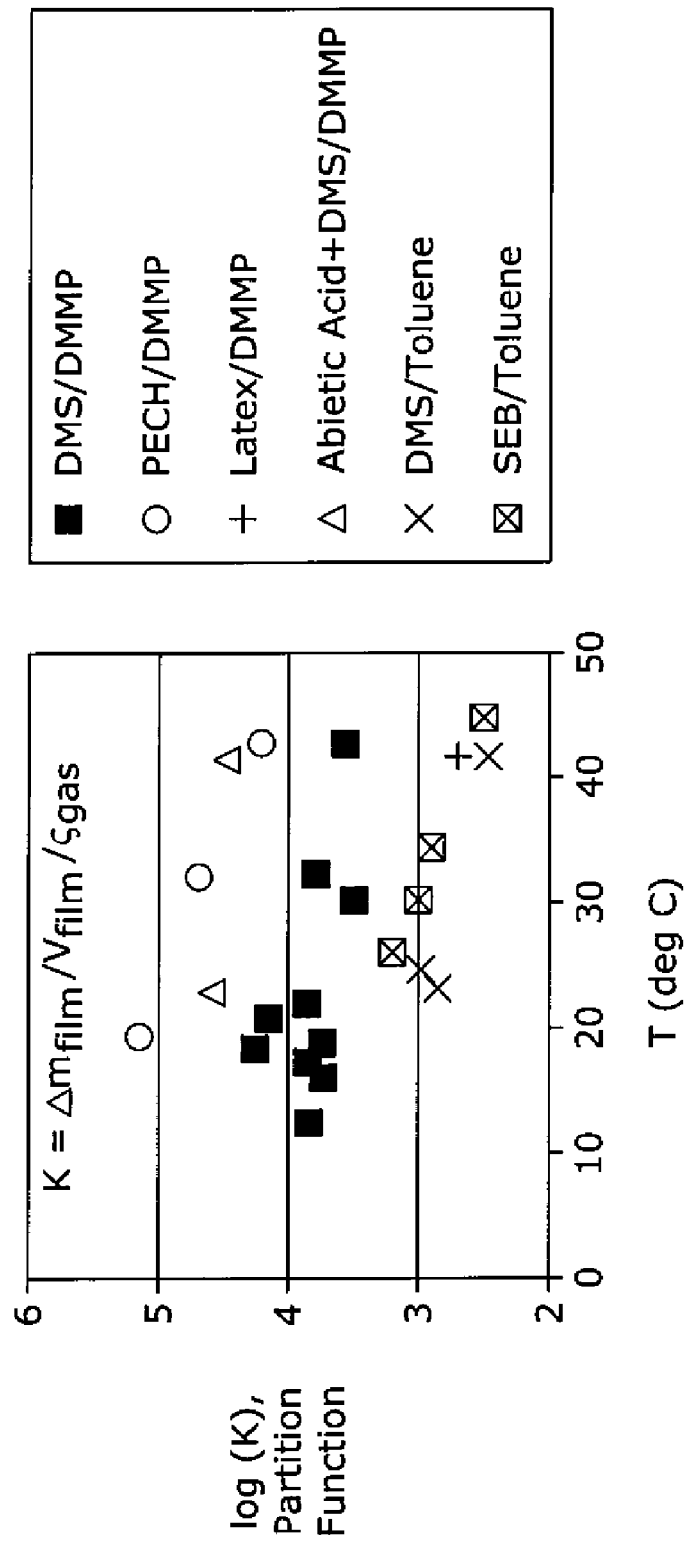
FIG. 9 is a plot of results of some materials as they relate to partition equilibria.
Figure 11:
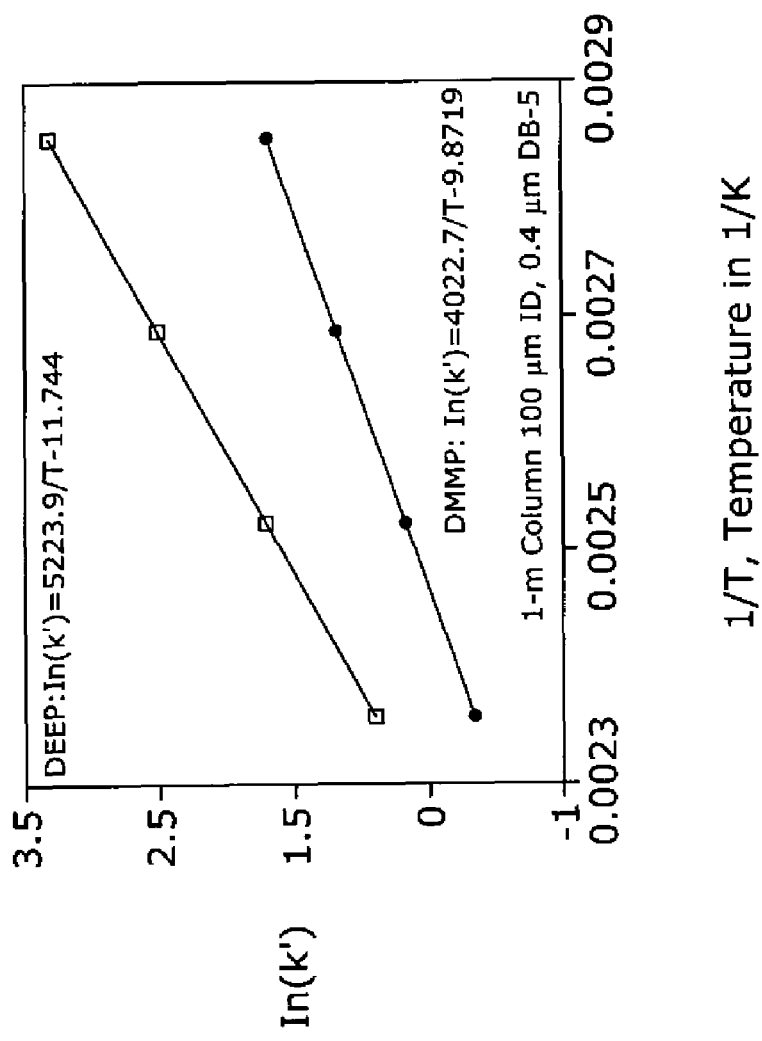
FIG. 11 shows retention time data relative to a column with DB-5 for DEEP and DMMP.

One may evaluate non-porous-film type CIDs. An ability to dissolve gaseous analytes into the structure of a polymer may be given by the solubility mass fraction, μ, which is closely related to the partition function or equilibrium where μ=m (vap-in-film)/m(film)=Δm(film)/V(film)/ρ(film), or, if viewed from the gas side, the partition function, K=Δm(film)/V(film)/ρ(vap)=μ·ρ(film)/ρ(vap), both of which may be listed in the table of FIG. 8. The solubility of gases in polymers may be discussed from a theoretical vantage point, and the experimental results of toluene and DMMP uptake in several polymers may be noted with partition equilibria or coefficients, K=Δm/V(film)/ρ(vap), at room temperature, ranging from 1000 to 100,000 as shown in a graphical plot in FIG. 9, and with some numerical examples at room temperature given in a table in FIG. 10, for vapor-(non-porous) polymer pairs. In the table, PDMS=polydimethylsiloxane, PECH=polyepichlorohydrin, Latex~polybutylene, ABACD=abietic acid, SEB=styrene/ethylene-butylene (powder), DMMP=dimethyl methylphosphonate, DEEP=diethyl ethylphosphonate, and DB-5=PDMS+5% phenyl substitution, a common GC film. As to DB-5, K=β·k', with k' may be from retention times (corrected for a temperature change from the experimental value of 100° C. to 25° C., see FIG. 11) for a column with 100 μm ID and 0.4 μm film thickness, β=61.7. FIG. 11 shows retention time and k'=($t_r$−$t_o$)/$t_o$ (plotted as ln(k')) versus 1/T (temperature in 1/K), for DEEP and DMMP.

As anticipated roughly by Raoult's law, the values for the more volatile compounds (toluene relative to DMMP) may be much lower, and those for smaller, more volatile molecules like hexane, may be lower still. The GC-film DB-5 appears to adsorb less gas than the other polymers noted, despite chemical similarities between PDMS and DB-5 and apparently widely diverging values. A significant point is that the estimated partition equilibrium constants for various analytes on the present porous sensor film with values of $t_4$, $\rho_{La}$ and $\rho_{ga}$ yield saturation k-values which may be worthy of note, as indicated in a table of FIG. 12. That table reveals partition coefficients derived for porous NG-E films of an 800 m²/g specific surface area.

For the table of FIG. 12, the "quasi K-values at boiling point" may be computed for an assumed monomolecular (liquid analyte) film inside all pores, which may then be converted to an equivalent analyte gaseous density fraction outside the pores but within the overall confines of the porous film. With the temperature dependence of k', which may also hold for K=k'·β, then the K-values may be converted from boiling point to 22° C. The so-obtained equivalent K-values (22° C.) should then be comparable to K-values for non-porous films in the table of FIG. 10. A comparison of these tables appear to show that the alkanes of increasing molecular weight might increase as expected, and that the analyte K-values in the porous film may be generally higher than those in non-porous films.

Large partition coefficients may enable analytes to concentrate in the film at K-times greater concentration than the one in the gas phase, thus reaching monomolecular film coverage before reaching a 100% gas-phase concentration. Therefore, the low-vapor pressure analytes of K~100,000 may be detected at 1 ppm gas phase concentrations with a capacitance sensitivity, δC~0.008 pF, rather than estimates of 0.08·10⁻⁶ pF, corresponding to K~1.

The present device may involve a monolithic micro GC pre-concentrator 121, separator 123 (FIGS. 15 and 16), TCD (thermal conductivity detector) 115, 118, flow sensor 122, p and T sensors, and a "thin-film" gas detector, e.g., CID 10. The present device may incorporate a monolithic micro GC system with a "thin-film" gas detector, in which this thin film may be the same active material in the three micro GC operations—pre-concentration, separation and CID, after a spin-coat application on one wafer, which forms one of the channel walls of, for example, concentrator 121 and/or separator 123. The micro GC may be a PHASED MGA 110. The noted "thin-film" material may consist of a porous film such as NGE (nanoglass-E), NGE+TA (toughening agent) or GX-3P as the with TA materials, available from Honeywell International Inc., rather than non-porous material films.

An advantage of the CID 10 may include greater sensitivity and speed combination than conventional CIDs, as provided by the large-surface area of the open-pore film, which enables analyte to more rapidly adsorb or dissolve into and desorb from the film 15 in this CID 10, than with a film of equal mass without pores. Another advantage may include the capability of one and the same GC stationary film to serve for pre-concentration and separation (of devices 121 and 123, respectively), as well as for gas detection, i.e., to observe the elution time and the peak area, to identify and quantify each analyte, respectively. Further, an application of the porous film via spin-coat on just one wafer to form one of the channel walls, may keep fabrication costs lower than fabrication involving coating of all channel walls.

Separation performance of GC columns with partial stationary phase coverage may be noted. Because k' depends on i.e., the ratio of gas/stationary phase volumes, stationary film temperature, and the stationary film thickness, then analyte molecules near the uncoated, wall may tend to elute without any retention (k'=0), whereas analyte molecules near the coated part of the column may be retained and correspond to k'>0, each of which is expected to result in significant deterioration of achievable separation efficiency. Countering this effect may be a rapid and short time diffusion between the walls of the (square) column. It may be calculated that an increase in plate height and associated loss in resolution in rectangular channels with only one or two coated walls coated, relative to columns with the four walls coated, shows that (the table of FIG. 13) for the square channels with one coated wall, the increased plate height is a factor of 1.50 relative to one with all walls coated, and a factor of 1.92 relative to a cylindrical column. These calculations appear to omit temperature effects. The table appears to concern separation impedances for pressure-driven systems. The retention factor k' may equal=4. Codes in first column may be as follows: "OT"=open cylindrical; "BT"=coating at bottom and top; "AL"=coating at all walls; "BO"=coating at bottom wall only; numbers by the codes refer to width-to-height ratio, $\phi$; "NE"=edge effects neglected; $u_m$=mean gas velocity; $v_m$=reduced gas velocity; $h=H/d_c$=reduced plate height; H=plate height, $d_c$=column ID; and $\Phi$=permeability factor.

Figure 14:
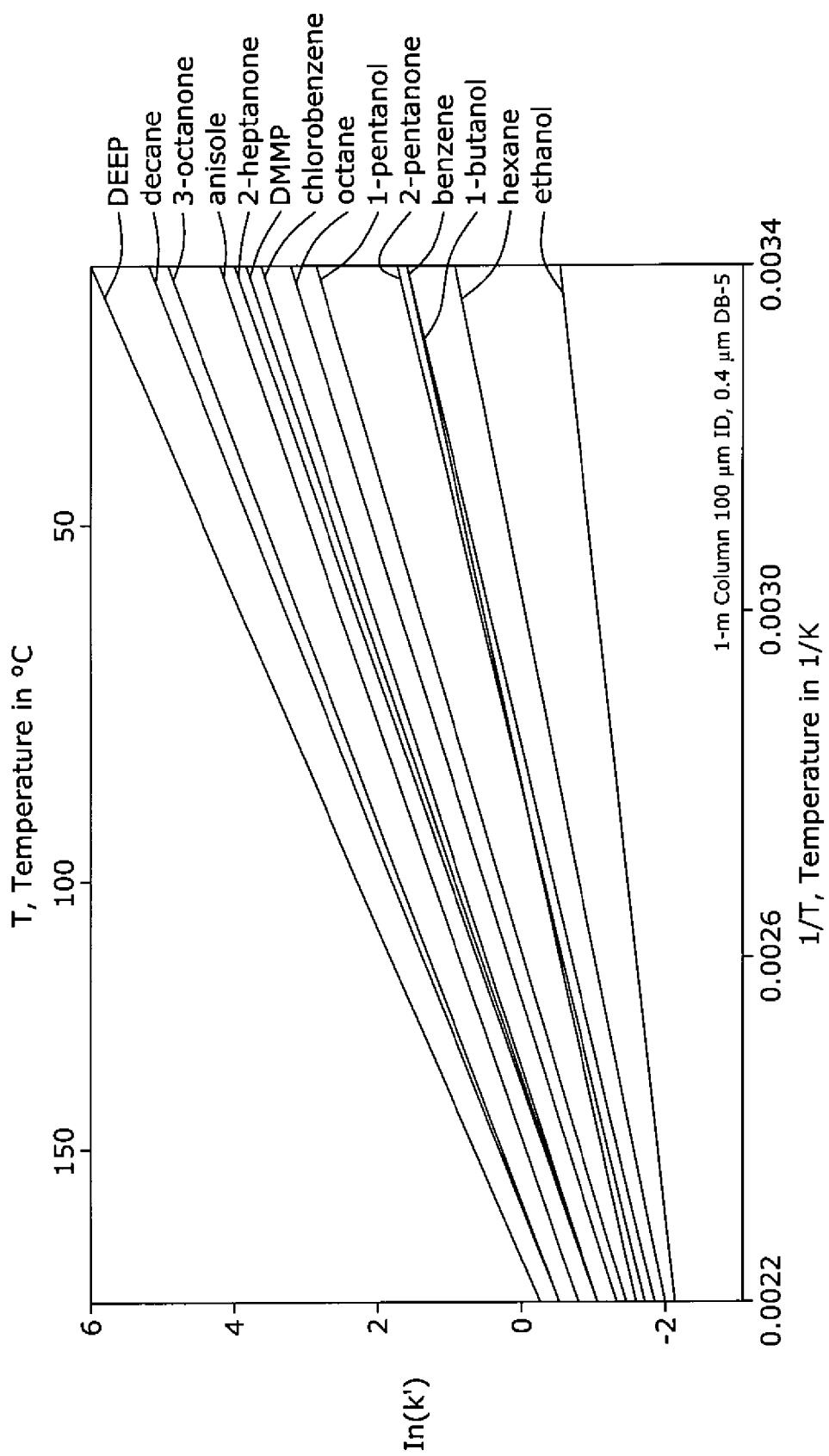
FIG. 14 is a graph is a graph of retention time for a number of analytes in a column having one regularly coated and heated wall and thinly coated, unheated remaining walls.

Temperature effects may be noted. Because the PHASED MGA columns may operate with temperature control of just one wall, temperature ramping, as needed to achieve high-speed analyses, can cause temperature gradients between the heated "wall" and the other uncoated ones. Fortunately, one may take advantage of the temperature-dependence of k' by applying a much thinner "coating" to the unheated walls, e.g., in the form of a thin "deactivation" film, which should exhibit smaller k'-values. During ramping, the lower temperatures of the cooler walls may qualitatively increase k'-values to approach the hot-wall values. If one selects the coating thicknesses carefully and remembering (FIG. 14) that for every 17° C. temperature drop, k' may approximately double or triple its value. FIG. 14, like FIG. 11, shows the retention time and $k'=(t_r-t_o)/t_o$ (plotted as ln(k')) versus 1/T, for a number of analytes.

Performance of a GC separation column may be expressed by a performance index, $\pi$:

$$\pi = N^2/(t_o \Delta p),$$

where N=number of theoretical plates, $t_o$=elution time for unretained peak, and $\Delta p$=pressure drop; and in terms of its reduced plate height, h=H/d, which may have a theoretical minimum of h=1, and d=capillary ID.

Other polymers, such as Nafion™, a proton-conducting, perfluoro-polymer, may be considered as material for a polymer film for the CID 10.

The invention may incorporate a channel or channels for a flow of a sample along a membrane that supports heaters and a stationary phase for sample analysis. The channel or channels may be an integral part of a micro fluid analyzer. The analyzer may have a pre-concentrator (PC) (viz., concentrator) and chromatographic separator (CS) that incorporates the channel or channels.

Figure 15:
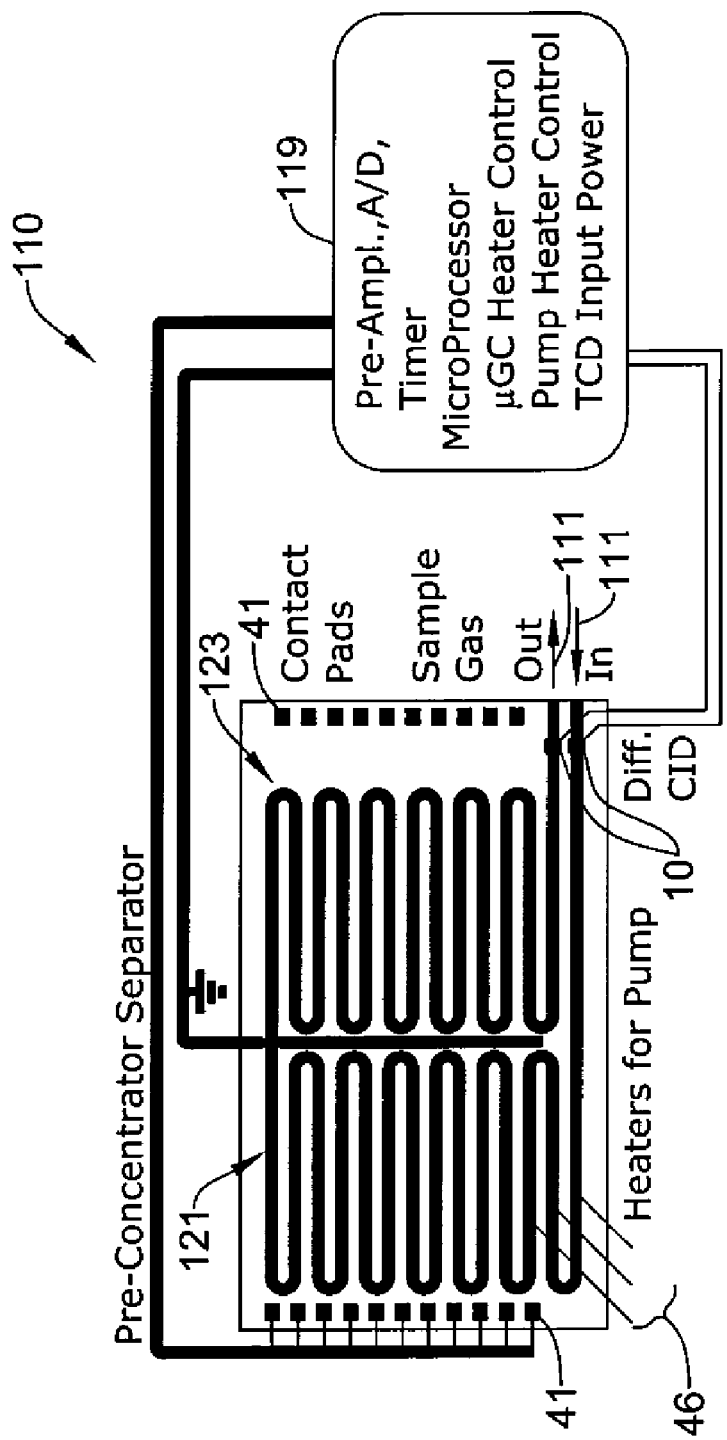
FIG. 15 shows an illustrative example of chemical impedance detectors of FIG. 2 situated in a fluid analyzer.

FIG. 15 shows a pre concentrator 121 and a separator 123 for a fluid analyzer 110. A CID 10 may be situated at an inlet of a pre concentrator 121 and an outlet of a separator 123. The CIDs 10 may be connected in a differential mode. A sample 111 may be moved with a thermal pump 46 in pre concentrator 121. The pump could instead be in the separator 123. The thermal pump 46 may have three heaters receiving sequenced energizing signals to provide heat pulses by the heaters in a fashion to move the sample fluid 111 through the pre concentrator 121 and separator 123. Other kinds of thermal pumps may be used, or an ordinary pump 116 (like that in FIG. 16) may be used. A controller 119 may provide signals to the pump 46, and to heaters in the pre concentrator 121 and separator 123 via contact pads 41. Controller 119 may process signals from the CIDs 10, and other detectors and flow sensor(s) (FIG. 16). Controller 119 may have, for instance, a pre amplifier, an analog-to-digital converter (and vice versa), a timer, and a microprocessor. The microprocessor may manage and process signals from the CIDs 10, flow sensor(s), TCDs, and so on, and provide signals for power to the heaters, including the pump, and to detectors (e.g., TCDs) and sensors as needed.

FIG. 16 is a system view of a fluid analyzer which may be a phased heater array structure for enhanced detection (PHASED) micro gas analyzer (MGA) 110. It reveals certain details of the micro gas apparatus 110 which may encompass the specially designed channel described herein. The PHASED MGA 110, and variants of it, may be used for various chromatography applications.

Sample stream 111 may enter input port 112 to the first leg of a differential thermal-conductivity detector (TCD) (or other device) 115. A pump 116 may effect a flow of fluid 111 through the apparatus 110 via tube 117. There may be additional or fewer pumps, and various tube or plumbing arrangements or configurations for system 110 in FIG. 16. Fluid 111 may be moved through a TDC 115, concentrator 121, flow sensor 122, separator 123 and TDC 118. Controller 119 may manage the fluid flow, and the activities of concentrator 121 and separator 123. Controller 119 may be connected to TDC 115, concentrator 121, flow sensor 122, separator 123, TDC 118, and pump 116. Data from detectors 115 and 118, and sensor 122 may be sent to controller 119, which in turn may process the data. The term "fluid" may refer to a gas or a liquid, or both.

Figure 17:
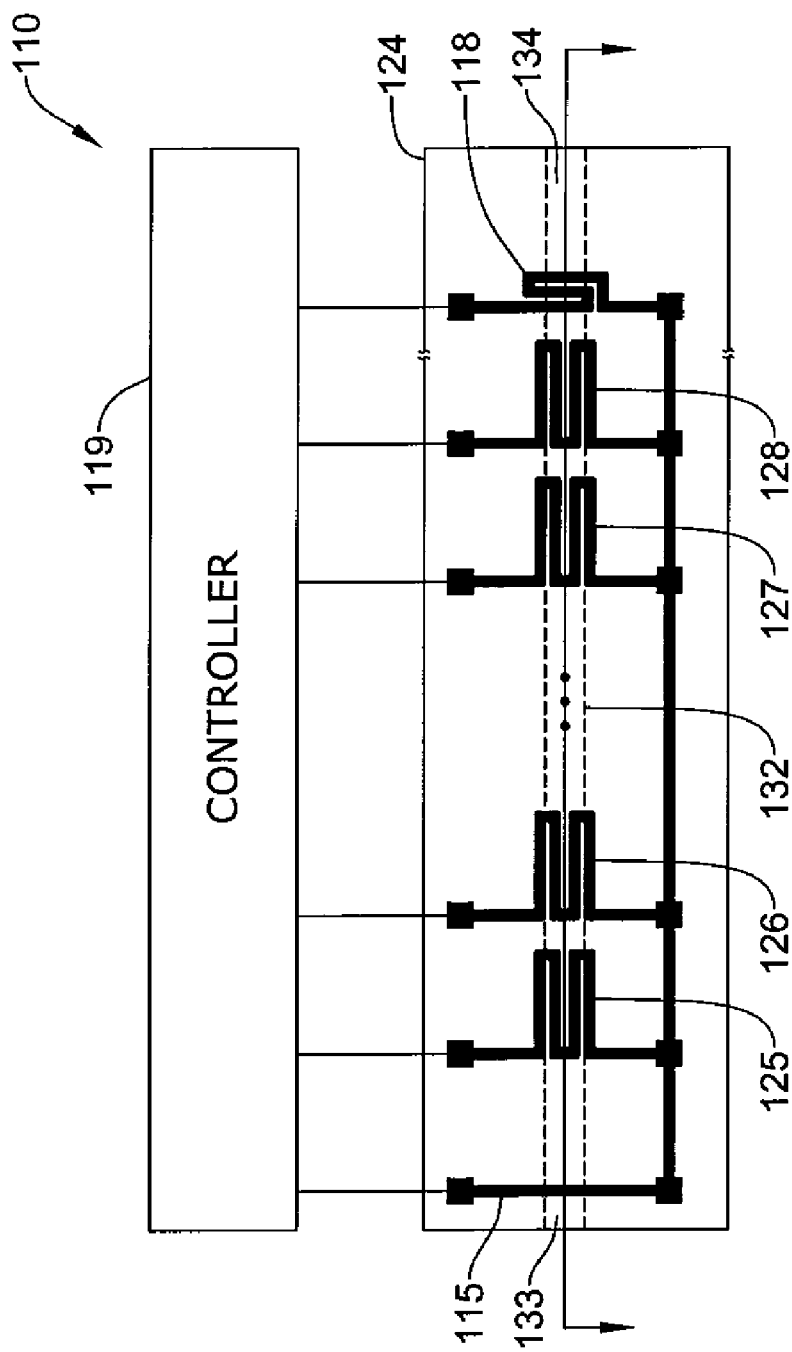
FIG. 17 shows a top view of a phased heater arrangement.

FIG. 17 is a schematic diagram of part of the sensor apparatus 110 representing a heater portion of concentrator 121 and/or separator 123 in FIG. 16. This part of sensor apparatus 110 may include a substrate or holder 124 and controller 119. Controller 119 may or may not be incorporated into substrate 124. Substrate 124 may have a number of thin film heater elements 125, 126, 127, and 128 positioned thereon. While only four heater elements are shown, any number of heater elements may be provided, for instance, between two and one thousand, but typically in the 20-100 range. Heater elements 125, 126, 127, and 128 may be fabricated of any suitable electrical conductor, stable metal, alloy film, or other material. Heater elements 125, 126, 127, and 128 may be provided on a thin, low-thermal mass, low-in-plane thermal conduction, membrane, substrate or support member 124, as shown in FIGS. 17 and 18.

Figure 18:
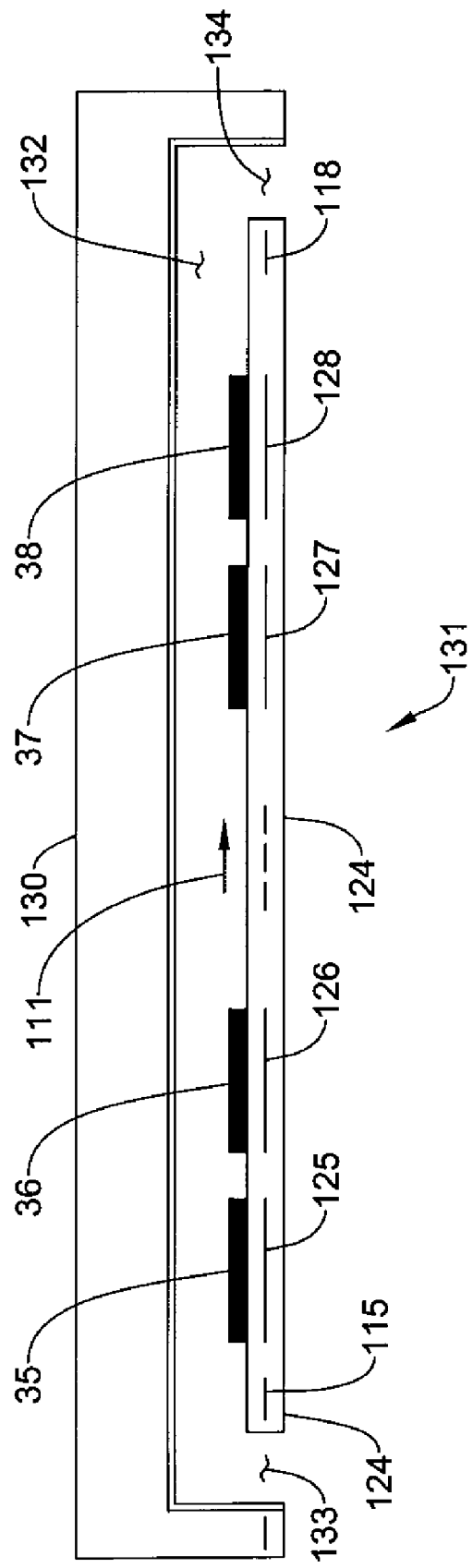
FIG. 18 is a cross section view of the heater arrangement and associated interactive elements.

In FIG. 18, substrate 130 may have a well-defined single-channel phased heater mechanism and channel structure 131 having a channel 132 for receiving the sample fluid stream 111. The channel may be fabricated by selectively etching a silicon channel wafer substrate 130 near the support member 124. The channel may include an entry port 133 and an exhaust port 134.

The sensor apparatus 110 may also include a number of interactive elements inside channel 132 so that they are exposed to the streaming sample fluid 111. Each of the interactive elements may be positioned adjacent, i.e., for closest possible thermal contact, to a corresponding heater element. For example, in FIG. 18, interactive elements 35, 36, 37, and 38 may be provided on a surface of support member 124 in channel 132, and be adjacent to heater elements 125, 126, 127, and 128, respectively. There may be detectors 115 and 118 at the ends of channel 132.

There may be other channels having interactive film elements which are not shown in the present illustrative example. The interactive elements may films be formed from any number of substances commonly used in liquid or gas chromatography. Furthermore, the interactive substances may be modified by suitable dopants to achieve varying degrees of polarity and/or hydrophobicity, to achieve optimal adsorption and/or separation of targeted analytes.

The micro gas analyzer 110 may have interactive elements 35, 36, . . . , 37 and 38 fabricated with various approaches, such that there is a pre-arranged pattern of concentrator and separator elements are coated with different adsorber materials A, B, C, . . . (known in gas chromatography (GC) as stationary phases). Not only may the ratio of concentrator 121/separator 123 elements be chosen, but also which elements are coated with A, B, C, . . . , and so forth, may be determined (and with selected desorption temperatures) to contribute to the concentration and separation process. A choice of element temperature ramping rates may be chosen for the A's which are different for the B, C, . . . , elements. Versatility may be added to this system in a way that after separating the gases from the group of "A" elements, another set of gases may be separated from the group of "B" elements, and so forth.

Controller 119 may be electrically connected to each of the heater elements 125, 126, 127, 128, and detectors 115 and 118 as shown in FIG. 17. Controller 119 may energize heater elements 125, 126, 127 and 128 in a time phased sequence (see bottom of FIG. 19) such that each of the corresponding interactive elements 35, 36, 37, and 38 become heated and desorb selected constituents into a streaming sample fluid 111 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be sensed by detector 118 for analysis by controller 119.

Figure 19:
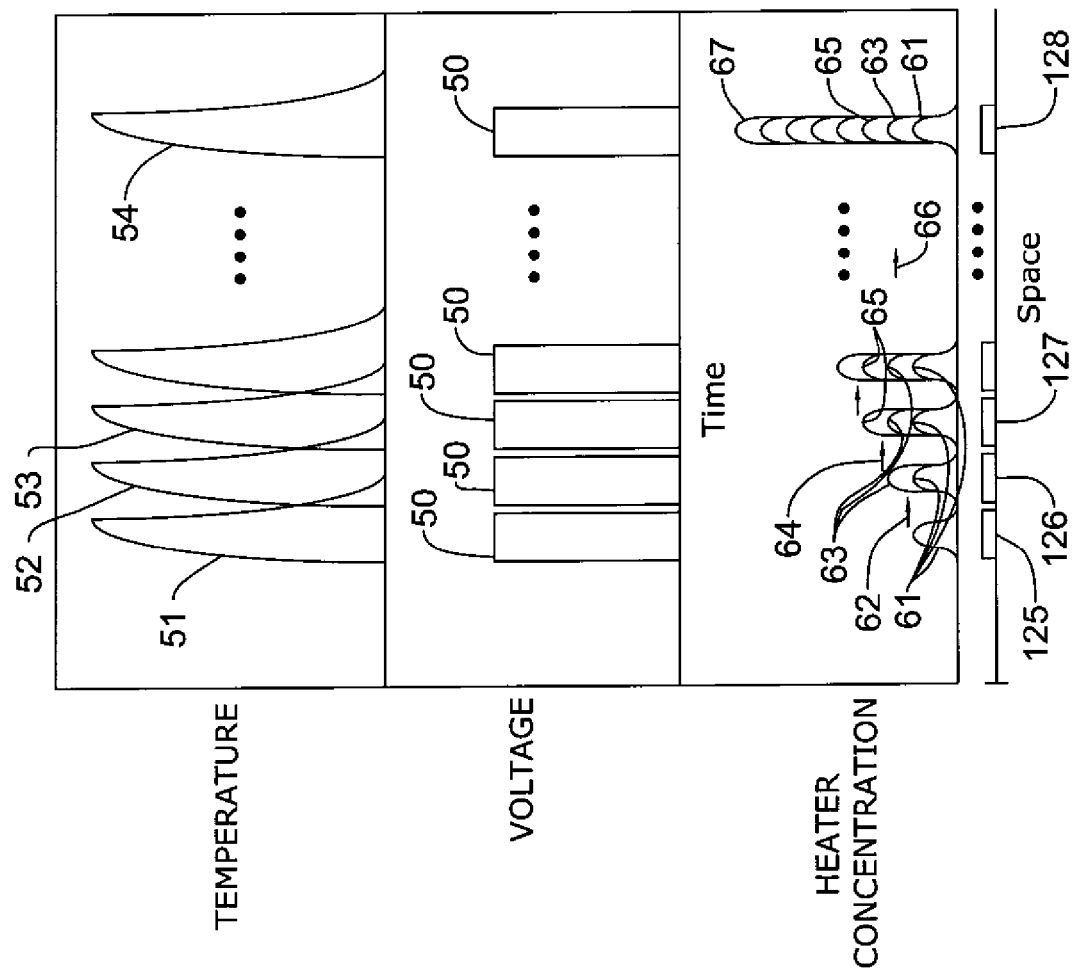
FIG. 19 shows graphs illustrating a phased heater arrangement operation.

FIG. 19 is a graph showing illustrative relative heater temperatures, along with corresponding concentration pulses produced at each heater element. As indicated herein, controller 119 may energize heater elements 125, 126, 127 and 128 in a time phased sequence with voltage signals 50. Time phased heater relative temperatures for heater elements 125, 126, 127, and 128 may be shown by temperature profiles or lines 51, 52, 53, and 54, respectively.

In the example shown, controller 119 (FIG. 17) may first energize heater element 125 to increase its temperature as shown at line 51 of FIG. 19. Since the first heater element 125 is thermally coupled to first interactive element 35 (FIG. 18), the first interactive element desorbs selected constituents into the streaming sample fluid 111 to produce a first concentration pulse 61 (FIG. 19), while no other heater elements are not yet pulsed. The streaming sample fluid 111 carries the first concentration pulse 61 downstream toward second heater element 126, as shown by arrow 62.

Controller 119 may next energize second heater element 126 to increase its temperature as shown at line 52, starting at or before the energy pulse on element 125 has been stopped. Since second heater element 126 is thermally coupled to second interactive element 36, the second interactive element also desorbs selected constituents into streaming sample fluid 111 to produce a second concentration pulse. Controller 119 may energize second heater element 126 in such a manner that the second concentration pulse substantially overlaps first concentration pulse 61 to produce a higher concentration pulse 63, as shown in FIG. 19. The streaming sample fluid 111 may carry the larger concentration pulse 63 downstream toward third heater element 127, as shown by arrow 64.

Controller 119 may then energize third heater element 127 to increase its temperature as shown at line 53 in FIG. 19. Since third heater element 127 is thermally coupled to the third interactive element 37, the third interactive element 37 may desorb selected constituents into the streaming sample fluid to produce a third concentration pulse. Controller 119 may energize the third heater element 127 such that the third concentration pulse substantially overlaps the larger concentration pulse 63, provided by the first and second heater elements 125 and 126, to produce an even larger concentration pulse 65. The streaming sample fluid 111 may carry this larger concentration pulse 65 downstream toward an "Nth" heater element 128, as shown by arrow 66.

Controller 119 may then energize "N-th" heater element 128 to increase its temperature as shown at line 54. Since "N-th" heater element 128 is thermally coupled to an "N-th" interactive element 38, "N-th" interactive element 38 may desorb selected constituents into streaming sample fluid 111 to produce an "N-th" concentration pulse. Controller 119 may energize "N-th" heater element 128 in such a manner that the "N-th" concentration pulse substantially overlaps the large concentration pulse 65 as provided by the previous N−1 interactive elements, to produce a larger concentration pulse 67. The streaming sample fluid 111 may carry the resultant "N-th" concentration pulse 67 to either a separator 123 and/or a detector 118.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. An impedance detector comprising:
a substrate;
a dielectric layer situated on the substrate;
a first electrode situated on the dielectric layer;
a second electrode situated on the dielectric layer; and
a polymer layer situated on a portion of the first electrode, a portion of the second electrode, and an area of the dielectric layer between the first electrode and the second electrode; and
wherein:
the first and second electrodes are interdigitated electrodes having a height;
the polymer layer is a low dielectric, porous, high surface area thin-film; and
the polymer layer disposed between the first electrode and the second electrode has a thickness approximately equal to the height of the first or second electrodes.

2. The detector of claim 1, wherein:
the first electrode comprises a first plurality of finger-like electrodes;
the second electrode comprises a second plurality of finger-like electrodes; and
wherein the first plurality of finger-like electrodes is intermeshed, but not in contact, with the second plurality of finger-like electrodes.

3. The detector of claim 2, wherein the electrodes comprise a porous structure.

4. The detector of claim 3, wherein the electrodes are low-height and low-width electrodes.

5. The detector of claim 1, wherein:
the substrate is silicon;
the dielectric layer is $SiO_2$;
the electrodes comprise conductive material; and
the polymer layer is a material having a low dielectric constant, porosity, and/or a high partition coefficient for a target analyte.

6. An impedance detector system, comprising:

a first interdigitated chemical impedance detector comprising:
- a substrate;
- a dielectric layer situated on the substrate;
- a first electrode situated on the dielectric layer;
- a second electrode situated on the dielectric layer; and
- a continuous polymer layer situated on the first electrode, the second electrode, and an area on the dielectric layer between the first and second electrodes, the polymer layer comprising a porous, high surface area thin-film; and
- wherein the polymer layer disposed between the first electrode and the second electrode has a thickness approximately equal to a height of the first or second electrodes; and a second interdigitated chemical impedance detector comprising:
- a substrate;
- a dielectric layer situated on the substrate;
- a first electrode situated on the dielectric layer;
- a second electrode situated on the dielectric layer; and
- a continuous polymer layer situated on the first electrode, the second electrode, and an area on the dielectric layer between the first and second electrodes, the polymer layer comprising a porous, high surface area thin-film; and
- wherein the polymer layer disposed between the first electrode and the second electrode has a thickness approximately equal to a height of the first and second electrodes.

7. The system of claim 6, wherein the first and second chemical impedance detectors are connected in a differential mode.

8. The system of claim 7, wherein:
the first chemical impedance detector is exposable to an analyte; and
the second impedance detector is exposable to a reference sample, which may contain a different concentration of the analyte.

9. The system of claim 7, wherein the differential mode is an AC-coupled mode.

10. The system of claim 6, wherein:
the first electrode of the first chemical impedance detector comprises a first plurality of finger-like electrodes;
the second electrode of the first chemical impedance detector comprises a second plurality of finger-like electrodes;
the first electrode of the second impedance detector comprises a third plurality of finger-like electrodes;
the second electrode of the second chemical impedance detector comprises a fourth plurality of finger-like electrodes;
the first plurality of finger-like electrodes is intermeshed, but not in contact, with the second plurality of finger-like electrodes; and
the third plurality of finger-like electrodes is intermeshed, but not in contact, with the fourth plurality of finger-like electrodes.

11. The detector of claim 10, wherein:
the polymer layer has a low dielectric constant;
the electrodes are low-height and low-width electrodes; and
the electrodes are porous.

12. The system of claim 6, further comprising:
an array of chemical impedance detectors; and
wherein:
the first and second chemical impedance detectors are in the array of chemical impedance detectors; and
each chemical impedance detector comprises:
- a substrate;
- a dielectric layer situated on the substrate;
- a first electrode situated on the dielectric layer;
- a second electrode situated on the dielectric layer; and
- a polymer situated on the first electrode, the second electrode, and an area on the dielectric layer between the first and second electrodes.

13. The system of claim 12, wherein:
the first electrode situated on the dielectric layer comprises a first plurality of low-height and low-width electrodes;
the second electrode of the chemical impedance detector comprises a second plurality of low-height and low-width electrodes; and
the first plurality of low-height and low-width electrodes is intermeshed, but not in contact, with the second plurality of low-height and low-width electrodes.

* * * * *